United States Patent [19]

Sasaki et al.

[11] Patent Number: 4,769,479

[45] Date of Patent: Sep. 6, 1988

[54] HYDROXYPHENYLPROPIONIC ACID ESTER WITH NOVEL CRYSTALLINE STRUCTURE AND PRODUCTION THEREOF

[75] Inventors: Manji Sasaki, Ibaraki; Chinehito Ebina, Minoo; Haruki Okamura, Osaka; Shinichi Yachigo, Toyonaka; Tamaki Ishii, Suita, all of Japan

[73] Assignee: Sumitomo Chemical Company, Limited, Osaka, Japan

[21] Appl. No.: 868,743

[22] Filed: May 30, 1986

[30] Foreign Application Priority Data

Jun. 21, 1985 [JP] Japan .................................. 60-136272
Aug. 29, 1985 [JP] Japan .................................. 60-190457
Feb. 26, 1986 [JP] Japan .................................. 61-40639

[51] Int. Cl.$^4$ .......................................... C07D 319/04
[52] U.S. Cl. .................................................. 549/335
[58] Field of Search ......................................... 549/335

[56] References Cited

U.S. PATENT DOCUMENTS 4,576,734 3/1986 Ishii et al. ............................ 252/404

FOREIGN PATENT DOCUMENTS

25826 2/1984 Japan .
231089 12/1984 Japan .

Primary Examiner—Nicky Chan
Attorney, Agent, or Firm—Wenderoth, Lind & Ponack

[57] ABSTRACT

3,9-bis{2-[3-(3-tert-butyl-4-hydroxy-5-methylphenyl)propionyloxy]-1,1-dimethylethyl}-2,4,8,10-tetraoxaspiro[5.5]undecane having a novel crystalline structure which, when subjected to Cu-K$_\alpha$ X-ray diffraction, shows sharp X-ray diffraction peaks at angles of diffraction, $2\theta = 4.2°$ and $2\theta = 10.6°$. Also provided is a method for producing this compound.

1 Claim, 5 Drawing Sheets

HYDROXYPHENYLPROPIONIC ACID ESTER WITH NOVEL CRYSTALLINE STRUCTURE AND PRODUCTION THEREOF

The present invention relates to 3,9-bis{2-[3-(3-tert-butyl-4-hydroxy-5-methylphenyl)propionyloxy]-1,1-dimethylethyl}-2,4,8,10-tetraoxaspiro[5.5]undecane (hereinafter referred to as hydroxyphenylpropionic acid ester) represented by the structural formula (I) having a novel crystalline structure:

It is well known that the hydroxyphenylpropionic acid ester represented by the structural formula (I) can effectively be used to prevent various kinds of synthetic resin from deterioration such as softening, embrittlement, surface crack, discoloration, etc. caused by the action of heat, light and oxygen at the time of processing and use [Japanese Patent Application Kokai (Laid-Open) Nos. 25826/1984 and 231089/1984]. As such synthetic resins, there may be mentioned polyolefins such as polyethylene, polypropylene, etc., styrene series synthetic resins such as polystyrene, impact-resistant polystyrene, ABS, etc., engineering plastics such as polyacetal, polyamide, etc., and polyurethane.

Previously, the present inventors found that the hydroxyphenylpropionic acid ester represented by the structural formula (I) exists in two forms, one being in the form of a glassy substance having a melting point of about 45° C. to about 55° C. (hereinafter referred to as γ-crystal) and the other being in the form of white crystals having a melting point of about 104° C. to about 109° C. (hereinafter referred to as αβ-crystal).

Figure 4:
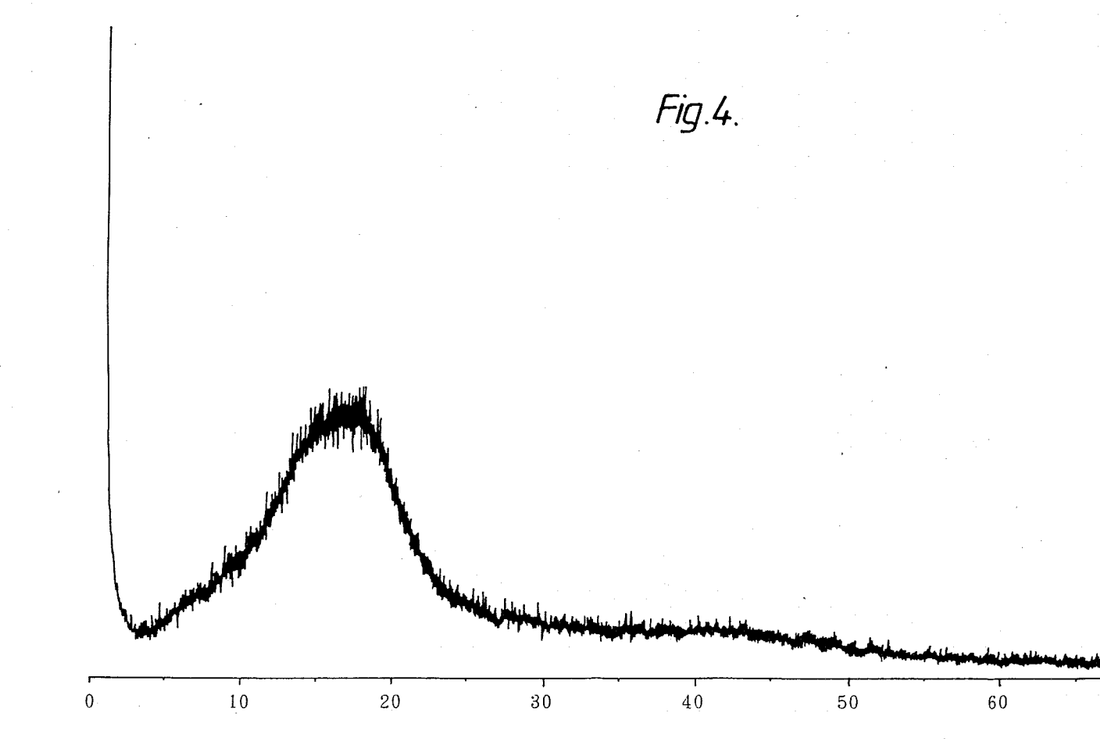
FIG. 4 is the X-ray diffraction pattern of the highly viscous substance (γ-crystal) obtained in Reference example 1.

The γ-crystals were obtained by melting a mixture of the ester (I) and impurities resulting from the production reaction, or the ester (I) of improved purity obtained by purification by column chromatography, etc., and then rapidly cooling the melt without using a solvent, and the melting point was in the range of from about 45° C. to about 55° C. The Cu-K$_\alpha$ X-ray diffraction pattern of the γ-crystals was as shown in FIG. 4.

Figure 2:
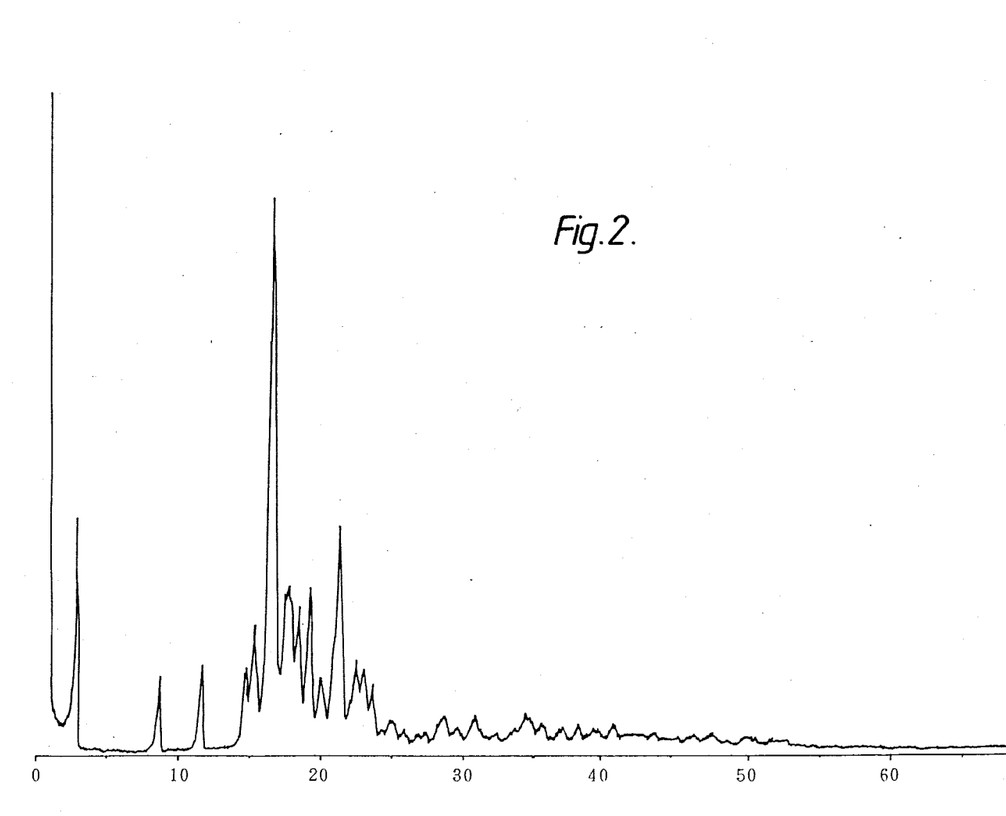
FIGS. 2 and 3 are the X-ray diffraction patterns of the crystals (αβ-crystal) obtained in Comparative examples 2 and 5, respectively.
Figure 3:
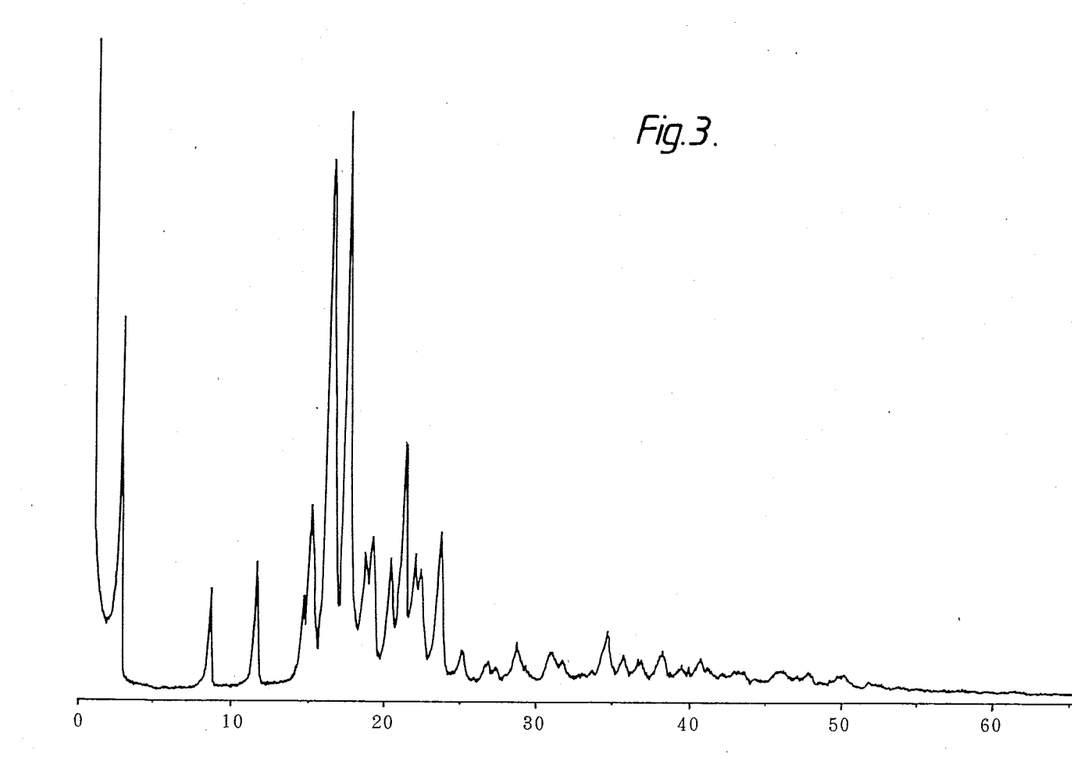

The αβ-crystals were obtained when the recrystallization method with n-hexane for 3,9-bis{2-[3-(3,5-di-tert-butyl-4-hydroxyphenyl)propionyloxy]-1,1-dimethylethyl}-2,4,8,10-tetraoxaspiro[5.5]undecane represented by the structural formula (II) (disclosed in the foregoing Japanese Patent Application Kokai No. 25826/1984), having a similar structure to that of the hydroxyphenylpropionic acid ester of the present invention represented by the foregoing structural formula (I), was applied as such to said ester (I), and the melting point was in the range of from about 104° C. to about 109° C. The Cu-K$_\alpha$ X-ray diffraction pattern of the αβ-crystals was as shown in FIGS. 2 and 3. Generally, the αβ-crystals seem to be obtained as a mixture of two or more forms having different crystalline structures, and the X-ray diffraction pattern varies as shown by FIGS. 2 and 3 depending upon the mixing ratio of the different forms. The melting point of the crystals sometimes is lowered a little or becomes wide in its range by reduction in purity, like usual compounds.

Thus, the present inventors' study has shown that the hydroxyphenylpropionic acid ester represented by the structural formula (I) takes either one of the αβ- or γ-crystal structure, and those other than these crystalline structures have not been known.

However, in producting these αβ- and γ-crystals on commercial scales, there have been many difficult problems, and only unsatisfactory results have been obtained.

For example, in the production of the αβ-crystals with, particularly, n-hexane as a recrystallization solvent, scaling of the recrystallization apparatus is remarkable, and also the purification effect is low because of a small solubility difference between the ester of the structural formula (I) and impurities contained in the mixture to be purified. This recrystallization method was therefore disadvantageous to use in commercial-scale purification.

With respect to the γ-crystals, the purification effect cannot be expected at all from the mixture of said ester (I) and impurities which results from the production reaction. Column chromatography is effective as a purification method, but it cannot be used as a large-scale commercial purification method for economical reasons.

It has therefore been considered to be very difficult to produce the hydroxyphenylpropionic acid ester represented by the structural formula (I) with ease and in high purity on a commercial scale.

The present inventors have extensively studied to solve these problems, and as a result, found that by carrying out the crystallization under a specific condition using a specific recrystallization solvent, the hydroxyphenylpropionic acid ester represented by the structural formula (I), with excellent quality and completely different in the crystalline structure from the conventional ones, can be obtained simply and economically, and also that the crystals thus obtained are higher in the melting point than the αβ- and γ-crystals, so that they can be used more advantageously. The present inventors have thus attained the present invention.

Thus the present invention is to provide the hydroxyphenylpropionic acid ester represented by the structural formula (I) having a novel crystalline structure which shows sharp X-ray diffraction peaks at angles of diffraction, $2\theta=4.2°$ and $2\theta=10.6°$, and $Cu-K_\alpha$ X-ray diffraction, and also to provide an advantageous method for producing said ester on a commercial scale.

The hydroxyphenylpropionic acid ester of the present invention represented by the structural formula (I) having a novel crystalline structure (hereinafter referred to as δ-crystal) has a diffraction pattern as shown in Table 1 and FIG. 1, in $Cu-K_\alpha$ X-ray diffraction.

Figure 1:
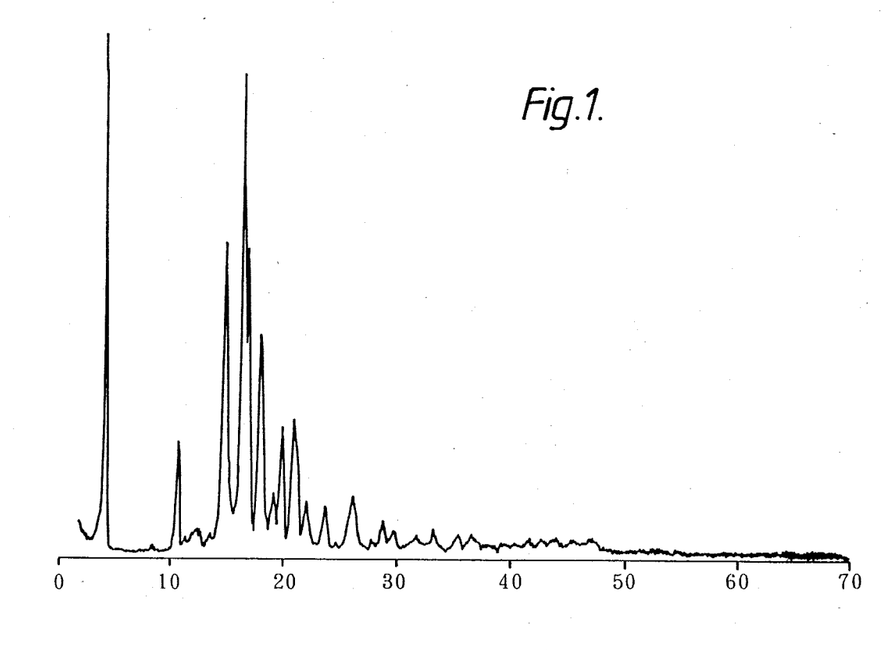
FIG. 1 is the X-ray diffraction pattern of the novel crystals (δ-crystal) of the present invention obtained in Example 1.

The δ-crystals of the present invention have a melting point in the range of from about 124° C. to about 127° C., and its $Cu-K_\alpha$ X-ray diffraction pattern, shown in Table 1 and FIG. 1, has sharp diffraction peaks, particularly, at $2\theta=4.2°$ and $2\theta=10.6°$, for which reason the crystals can easily be distinguished from the αβ- and γ-crystals. The melting point of the δ-crystals, of course, sometimes is lowered a little below or the range becomes wider than the melting point range described above, by reduction in purity like usual compounds, and it is generally in the range of from 118° C. to 126° C. when prepared by the δ-crystal production method of the present invention to be described below.

The δ-crystals of the present invention, because of the higher melting point than that of the αβ-crystals, shows an improved blocking property at the drying and crushing steps subsequent to the recrystallization step. The δ-crystals, surprisingly, have a lower solubility than that of the αβ-crystals (Table 2), and the compatibility with impurities produced at the same time by the production reaction is low so that the recrystallization yield is high and a high-purity product can be obtained easily. Further, the growth of the δ-crystals is easy as compared with the αβ-crystals, for which reason the δ-crystals can be obtained in large size crystals and have much improved filterability.

The foregoing excellent characteristics, and of course the presence of the δ-crystals of the present invention, could not be forecast from the prior art at all.

TABLE 1

| Angle of diffraction | | Relative |
|---|---|---|
| No. | 2 θ (degree) | strength (%) |
| 1 | 4.16 | 96 |
| 2 | 10.63 | 22 |
| 3 | 11.36 | 4 |
| 4 | 12.31 | 6 |
| 5 | 12.67 | 6 |
| 6 | 13.47 | 4 |
| 7 | 14.91 | 65 |
| 8 | 16.48 | 100 |
| 9 | 16.92 | 64 |
| 10 | 18.03 | 46 |
| 11 | 19.11 | 13 |
| 12 | 19.91 | 27 |
| 13 | 20.94 | 27 |
| 14 | 22.10 | 11 |
| 15 | 23.70 | 10 |
| 16 | 24.76 | 3 |
| 17 | 26.12 | 12 |
| 18 | 27.83 | 3 |
| 19 | 28.83 | 8 |
| 20 | 29.89 | 5 |
| 21 | 31.74 | 4 |
| 22 | 33.21 | 6 |
| 23 | 35.47 | 5 |
| 24 | 36.54 | 5 |
| 25 | 38.06 | 3 |
| 26 | 39.40 | 3 |

TABLE 1-continued

| Angle of diffraction | | Relative |
|---|---|---|
| No. | 2 θ (degree) | strength (%) |
| 27 | 41.58 | 4 |
| 28 | 44.10 | 4 |
| 29 | 45.57 | 4 |
| 30 | 46.83 | 4 |

TABLE 2

| Temperature (°C.) | Solubility (g/100 g cyclohexane) | |
|---|---|---|
| | αβ-Crystal | δ-Crystal |
| 20 | 0.2 | 0.06 |
| 30 | 0.5 | 0.1 |
| 40 | 1.4 | 0.2 |
| 50 | 4.1 | 0.5 |
| 55 | 8.5 | 1.1 |
| 60 | >60 | 2.1 |

The δ-crystals can easily be produced, for example, by dissolving the hydroxyphenylpropionic acid ester represented by the structural formula (I) in (1) a recrystallization solvent comprising a water-soluble solvent and water in an amount of 0 to 3 times by weight based thereon, or (2) a recrystallization solvent comprising a $C_5$–$C_{10}$ alicyclic hydrocarbon, and forming the crystals at a temperature of 40° C. or higher.

For the recrystallization, either one of (1) or (2) may be used. When the recrystallization solvent (1) is used, it may be a water-soluble solvent alone. However when water is mixed with such solvent the solubility can be lowered so that a temperature at which only the δ-crystals are formed may be further increased, as a result of which the growth of the crystals may be promoted and the filter-ability thereof can be improved.

Also, such mixing of water causes a reduction in the solubility to increase the crystallization yield, and in addition, is useful in improved safety against ignition and explosion. Consequently, such mixing of water is preferred industrially. The amount of water to be mixed varies depending upon the particular kind of solvent, but it is generally not more than 3 times by weight based on the water-soluble solvent. When the amount of water exceeds 3 times by weight, there is a tendency for the quality of the product such as purity, color, etc. to lower remarkably.

The water-soluble solvents to be used include alcohols, glycols, aliphatic ketones, aliphatic nitriles, alicyclic ethers, amides, tertiary amines, etc.

The recrystallization solvent wherein the water-soluble solvent is used will be explained below in more detail.

The alcohols are preferably those having 1 to 8 carbon atoms, and particularly preferably those having 1 to 3 carbon atoms. The amount of water to be mixed is preferably 0 to 0.4 time by weight based on the alcohol. Specific examples of the alcohol include methanol, ethanol, n-propanol, isopropanol, n-butanol, n-hexanol, 2-ethylhexanol, glycerin, etc., among which methanol and isopropanol are particularly preferred. The amount of water to be mixed is particularly preferably 0 to 0.3 time by weight for methanol, and 0 to 0.2 time by weight for isopropanol.

The glycols are preferably those having 2 to 6 carbon atoms, and specific examples include ethylene glycol, trimethylene glycol, diethylene glycol, triethylene glycol, etc. The amount of water to be mixed is preferably 0 to 0.3 time by weight based on the glycol.

The aliphatic ketones are preferably those having 3 to 6 carbon atoms, and specific examples include acetone, methyl ethyl ketone, diethyl ketone, methyl isobutyl ketone, etc., among which acetone is particularly preferred. The amount of water to be mixed is preferably 0 to 2 times by weight based on the ketone.

The aliphatic nitriles include acetonitrile, propionitrile, etc., and they are preferably mixed with water in an amount of 0 to 1 time by weight based on the nitrile.

Alicyclic ethers include 1,4-dioxane, tetrahydrofuran, etc., the amides include N,N-dimethylformamide, N,N-dimethylacetamide, N-methyl-2-pyrrolidone, etc., and the tertiary amines include triethylamine, pyridine, etc. These solvents are preferably mixed with water in an amount of of 0 to 3 times by weight based thereon.

Also, $C_5$-$C_{10}$ alicyclic hydrocarbons can be used alone as the recrystallization solvent, and their specific examples include cyclopentane, cyclohexane, methylcyclohexane, cyclooctane, cyclodecane, etc.

When any of the foregoing recrystallization solvents (1) and (2) is used, the temperature at which the crystals are formed is very important, and the temperature for the crystallization should be 40° C. or higher.

When the temperature is lower than 40° C., the desired δ-crystals are not obtained in a good yield and the purity is low, because the formed crystals are αβ-crystals only or a mixture of the αβ- and δ-crystals. In order to minimize the loss of the ester of the structural formula (I) remaining dissolved in the recrystallization solvent, it is of course allowable that the solution after the crystallization at a temperature of 40° C. or higher has substantially been finished is cooled far below said temperature and filtered.

The δ-crystals can also be produced by recrystallizing the hydroxyphenylpropionic acid ester represented by the structural formula (I) from a mixed solvent comprising a water-insoluble solvent except alicyclic or aliphatic hydrocarbons and an aliphatic hydrocarbon in an amount of 0 to less than 10 times by weight based on the water-insoluble solvent.

The water-insoluble solvent other than alicyclic or aliphatic hydrocarbons, as referred to herein, includes esters, aliphatic ethers, aliphatic halides, aromatic chlorides, aromatic hydrocarbons, etc. More specifically, there may be mentioned esters such as ethyl acetate, n-butyl acetate, dimethyl phthalate, di-n-butyl phthalate, etc., aliphatic ethers such as diethyl ether, diisopropyl ether, etc., aliphatic halides such as chloroform, carbon tetrachloride, 1,2-dichloroethane, 1,1,2,2-tetrachloroethane, etc., and aromatic chlorides such as chlorobenzene, dichlorobenzene, etc. Also, as the aromatic hydrocarbons, those having 7 to 12 carbon atoms are preferred, and specifically, there are given toluene, o-xylene, m-xylene, p-xylene, 1,2,3-trimethylbenzene, 1,2,4-trimethylbenzene, 1,3,5-trimethylbenzene, 1,2,4,5-tetramethylbenzene, ethylbenzene, cumene, o-cymene, m-cymene, p-cymene, o-diisopropylbenzene, m-diisopropylbenzene, p-diisopropylbenzene, etc.

When such water-insoluble solvent is used as the recrystallization solvent, the solubility of the αβ-crystals in this solvent is so high that the δ-crystals containing substantially no αβ-crystals can be obtained even at room temperature. Thus in this case, the temperature at which the crystals are to be formed is not particularly limited. In this case, by using the water-insoluble solvent in mixture with an aliphatic hydrocarbon in an amount of 0 to less than 10 times by weight based thereon, the solubility of the δ-crystals can be lowered, so that it becomes possible to carry out the crystallization at a higher temperature and also the crystallization yield can be increased. As such aliphatic hydrocarbon, those having 6 to 10 carbon atoms are preferred, and specifically, there may be exemplified n-hexane, n-heptane, n-octane, 2-methylheptane, n-decane, etc.

In any of the methods described above, the amount of the recrystallization solvent to be used is generally 0.5 to 10 times by weight based on the material to be subjected to the crystallization.

Recrystallization is carried out by completely dissolving the starting compound in the recrystallization solvent at the boiling point or a temperature lower than that, adding seed crystals as nucleus for crystallization if necessary, at a temperature corresponding to the solvent and then stirring the solution at the same temperature to form the crystals. In order to increase the crystallization yield, the solution, after the crystal formation has substantially been finished, is cooled to a much lower temperature if necessary, and the formed crystals are separated from the filtrate by a filter, washed and dried. Of course, it is also possible to apply decoloration treatment with activated carbon, active clay, silica gel, etc. in the course of the recrystallization operation.

Thus, the present invention provides the hydroxyphenylpropionic acid ester represented by the structural formula (I) having a novel and so far unknown crystalline structure. Also, by producing said ester in the form of the δ-crystals of the present invention, the ester of the structural formula (I), which has been difficult to obtain in high purity on the commercial scale by conventional methods, can be produced in a high yield on a commercial scale without any disadvantage in operation such as scaling of the apparatus, and in the form of white crystals superior in color, being quite satisfactory in both purity and practicability.

The present invention will be illustrated with reference to the following examples. The percentages (%) in the reference examples, examples and comparative examples are by weight unless otherwise specified.

REFERENCE EXAMPLE 1

To a 500-ml four-necked flask equipped with a stirrer, condenser, thermometer and nitrogen-introducing pipe were added 200.3 g (0.8 mole) of methyl 3-(3-tert-butyl-4-hydroxy-5-methylphenyl)-propionate and 60.88 g (0.2 mole) of 3,9-bis(2-hydroxy-1,1-dimethylethyl)-2,4,8,10-tetraoxaspiro[5.5]undecane, and the mixture was formed into solution by heating at 150° C. for 30 minutes with stirring in a nitrogen atmosphere. After adding 2.25 g (0.04 mole) of calcium oxide to this solution, the solution was heated to 190° C. and kept at the same temperature for 6 hours while distilling off formed methanol to complete the reaction.

After completion of the reaction, the reaction solution was diluted with toluene, neutralized with aqueous dilute hydrochloric acid and washed with water. After removing toluene by distillation, 97.1 g of methyl 3-(3-tert-butyl-4-hydroxy-5-methylphenyl)propionate, the starting material present in excess, were distilled off to obtain 148.3 g of a pale yellow highly viscous substance. Analysis of this highly viscous substance showed that it contained 96.4% of 3,9-bis{2-[3-(3-tert-butyl-4-hydroxy-5-methylphenyl)propionyloxy]-1,1-dimethylethyl}-2,4,8,10-tetraoxaspiro[5.5]undecane, the yield of this product being 96.5% based on 3,9-bis(2-hydroxy-1,1-dimethylethyl)-2,4,8,10-tetraoxaspiro[5.5]undecane, and also that said substance contained methyl 3-(3-tert-butyl-4-hydroxy-5-methylphenyl)propionate which was the starting material, and other by-products in the amounts of 1.2% and 2.4%, respectively.

This highly viscous substance, upon Cu-K$_\alpha$ X-ray diffraction analysis had an X-ray diffraction pattern as shown in FIG. 4 with no clear diffraction peak.

REFERENCE EXAMPLE 2

Procedure was carried out in the same manner as in Reference example 1 except that 2.25 g (0.02 mole) of potassium tert-butoxide was used in place of calcium oxide, and that reaction was completed at 150° C. under a pressure of 5 mmHg. The product was after-treated in the same manner as in Reference example 1. As a result, 92.5 g of methyl 3-(3-tert-butyl-4-hydroxy-5-methylphenyl)propionate, the starting material present in excess, was recovered, and 145.2 g of a brown highly viscous substance was obtained. Analysis of this highly viscous substance showed that it contained 87.5% of 3,9-bis{2-[3-(3-tert-butyl-4-hydroxy-5-methylphenyl)-propionyloxy]-1,1-dimethylethyl}-2,4,8,10-tetraoxaspiro[5.5]undecane, the yield of this product being 85.8% based on 3,9-bis(2-hydroxy-1,1-dimethylethyl)-2,4,8,10-tetraoxaspiro[5.5]undecane, and also that said substance contained methyl 3-(3-tert-butyl-4-hydroxy-5-methylphenyl)propionate which was the starting material, and other by-products in the amounts of 1.4% and 11.1%, respectively.

REFERENCE EXAMPLE 3

Procedure was carried out in the same manner as in Reference example 1 except that 0.46 g (0.02 mole) of lithium amide was used in place of calcium oxide, and that reaction was completed at 150° C. under a pressure of 5 mmHg. The product was after-treated in the same manner as in Reference example 1. As a result, 95.4 g of methyl 3-(3-tert-butyl-4-hydroxy-5-methylphenyl)propionate, the starting material present in excess, was recovered, and 145.8 g of a brown highly viscous substance was obtained. Analysis of this highly viscous substance showed that it contained 88.9% of 3,9-bis{2-[3-(3-tert-butyl-4-hydroxy-5-methylphenyl)propionyloxy]-1,1-dimethylethyl}-2,4,8,10-tetraoxaspiro[5.5]undecane, the yield of this product being 87.5% based on 3,9-bis(2-hydroxy-1,1-dimethylethyl)-2,4,8,10-tetraoxaspiro[5.5]undecane, and also that said substance contained methyl 3-(3-tert-butyl-4-hydroxy-5-methylphenyl)propionate which was the starting material, and other by-products in the amounts of 1.5% and 9.6%, respectively.

The highly viscous substances obtained in Reference examples 2 and 3 were subjected to Cu-K$_\alpha$ X-ray diffraction, and had the same X-ray diffraction pattern as shown in FIG. 4.

EXAMPLE 1

Fifty grams of the highly viscous substance obtained in Reference example 1 were dissolved in 212.5 g of methanol at 60° C. The resulting solution was cooled while adding 37.5 g of water with stirring, and 0.1 g of seed crystals was added at 50° C. After stirring the solution at the same temperature for further 2 hours to form crystals, the solution was cooled to 15° C. and stirred at the same temperature for 2 hours. The crystals obtained were filtered off on a glass filter, washed with a mixture of 170 g of methanol and 30 g of water previously cooled to 15° C. and dried to obtain 45.7 g of white crystals having a melting point of 124° C. to 126° C. Analysis of the white crystals showed that they contained 98.0% of the desired 3,9-bis{2-[3-(3-tert-butyl-4-hydroxy-5-methylphenyl)propionyloxy]-1,1-dimethylethyl}-2,4,8,10-tetraoxaspiro[5.5]undecane, and also that said crystals contained methyl 3-(3-tert-butyl-4-hydroxy-5-methylphenyl)propionate which was the starting material, and other by-products in the amounts of 0.7% and 1.3%, respectively.

These white crystals were subjected to Cu-K X-ray diffraction to obtain an X-ray diffraction pattern with sharp diffraction peaks at angles of diffraction, $2\theta = 4.2°$ and $2\theta = 10.6°$, as shown in FIG. 1.

EXAMPLES 2 TO 4

Recrystallization was repeated in the same manner as in Example 1 except that the methanol/water mixture was replaced by the same weight of each of 10% water-containing ethanol (Example 2), 10% water-containing isopropanol (Example 3) and 5% water-containing n-hexanol (Example 4). The results are shown in Table 3.

EXAMPLES 5 TO 7

Recrystallization was repeated in the same manner as in Example 1 except that the highly viscous substance was dissolved at 100° C. and that the methanol/water mixture was replaced with the same amount of each of 2-ethylhexanol only (Example 5), glycerin only (Example 6) and triethylene glycol only (Example 7), and that the crystals were formed at 80° C. and washed with the respective solvents. The results are shown in Table 3.

EXAMPLES 8 TO 15

Recrystallization was repeated in the same manner as in Example 1 except that the methanol/water mixture was replaced with the same weight of each of 50% water-containing acetone (Example 8), 30% water-containing methyl isobutyl ketone (Example 9), 50% water-containing acetonitrile (Example 10), 50% water-containing dioxane (Example 11), 50% water-containing tetrahydrofuran (Example 12), 70% water-containing N,N-dimethylformamide (Example 13), 60% water-containing N,N-dimethylacetamide (Example 14) and 50% water-containing pyridine (Example 15). The results are shown in Table 3.

EXAMPLE 16

Fifty grams of the highly viscous substance obtained in Reference example 1 was disolved in 250 g of cyclohexane at 70° C. The resulting solution was cooled with stirring, and 0.1 g of seed crystals were added at 50° C. Thereafter, the solution was stirred at the same temperature for further 15 hours to form crystals. The resulting crystals were filtered off at room temperature on a glass filter, washed with cyclohexane and dried at 40° C. under reduced pressure to obtain 46.0 g of white crystals having a melting point of 120° C. to 125° C. Analysis of the white crystals showed that they contained 98.5% of the desired 3,9-bis{2-[3-(3-tert-butyl-4-hydroxy-5-methylphenyl)propionyloxy]-1,1-dimethylethyl}-2,4,8,10-tetraoxaspiro[5.5]undecane and 1.5% of by-products, but that there was contained no methyl 3-(3-tert-butyl-4-hydroxy-5-methylphenyl)propionate which was the starting material.

EXAMPLES 17 AND 18

Recrystallization was repeated in the same manner as in Example 16 except that the highly viscous substances obtained in Reference example 2 (Example 17) and 3 (Example 18), respectively, were used in place of the highly viscous substance obtained in Reference example 1. The results are shown in Table 3.

EXAMPLES 19 TO 21

Recrystallization was repeated in the same manner as in Example 16 except that cyclohexane was replaced by each of methylcyclopentane (Example 19), methylcyclohexane (Example 20) and cyclooctane (Example 21). The results are shown in Table 3.

EXAMPLE 22

Fifty grams of the highly viscous substance obtained in Reference example 1 were dissolved in 75 g of toluene at 70° C. The resulting solution was cooled with stirring, and 0.1 g of seed crystals was added at room temperature. Thereafter, the solution was stirred at the same temperature for further 8 hours to form crystals. The solution was then cooled to −5° C. and stirred at the same temperature for further 2 hours. The resulting crystals were filtered off on a glass filter, washed with cold toluene and dried under reduced pressure to obtain 43.0 g of white crystals having a melting point of 122° C. to 125° C. Analysis of the white crystals showed that they contained 98.5% of the desired 3,9-bis{2-[3-(3-tert-butyl-4-hydroxy-5-methylphenyl)propionyloxy]-1,1-dimethylethyl}-2,4,8,10-tetraoxaspiro[5.5]undecane and 1.5% of by-products, but that there is contained no methyl 3-(3-tert-butyl-4-hydroxy-5-methylphenyl)propionate which was the starting material.

EXAMPLES 23 TO 30

Recrystallization was repeated in the same manner as in Example 22 except that 75 g of toluene was replaced by each of 100 g of ethylbenzene (Example 23), 150 g of cumene (Example 24), 150 g of p-cymene (Example 25), a mixture of 50 g of ethyl acetate and 150 g of n-hexane (Example 26), a mixture of 75 g of n-butyl acetate and 150 g of n-hexane (Example 27), a mixture of 150 g of di-n-butyl phthalte and 100 g of n-hexane (Example 28), a mixture of 50 g of chloroform and 150 g of n-hexane (Example 29) and a mixture of 150 g of 1,1,2,2-tetrachloroethane and 50 g of n-hexane (Example 30). For washing, the same solvents were used respectively. The results are shown in Table 3.

The white crystals obtained in the above Examples 2 to 30 were subjected to Cu-K$_\alpha$ X-ray diffraction to find that all the white crystals had the same X-ray diffraction pattern as shown in FIG. 1, and also that sharp X-ray diffraction peaks were observed in all cases at angles of diffraction, $2\theta = 4.2°$ and $2\theta = 10.6°$.

COMPARATIVE EXAMPLE 1

Recrystallization was carried out in the same manner as in Example 1 except that the methanol/water mixture was replaced by the same weight of 30% water-containing methanol, and that the crystal formation was conducted at 30° C. The result is shown in Table 3.

COMPARATIVE EXAMPLE 2

Recrystallization was carried out in the same manner as in Example 16 except that the crystal formation was conducted at 30° C. The result is shown in Table 3.

COMPARATIVE EXAMPLE 3

Recrystallization was carried out in the same manner as in Example 17 except that the crystal formation was conducted at 30° C. The result is shown in Table 3.

COMPARATIVE EXAMPLE 4

Recrystallization was carried out in the same manner as in Example 18 except that the crystal formation was conducted at 30° C. The result is shown in Table 3.

COMPARATIVE EXAMPLE 5

Recrystallization was carried out in the same manner as in Example 16 except that n-hexane was used in place of cyclohexane. The result is shown in Table 3.

Figure 5:
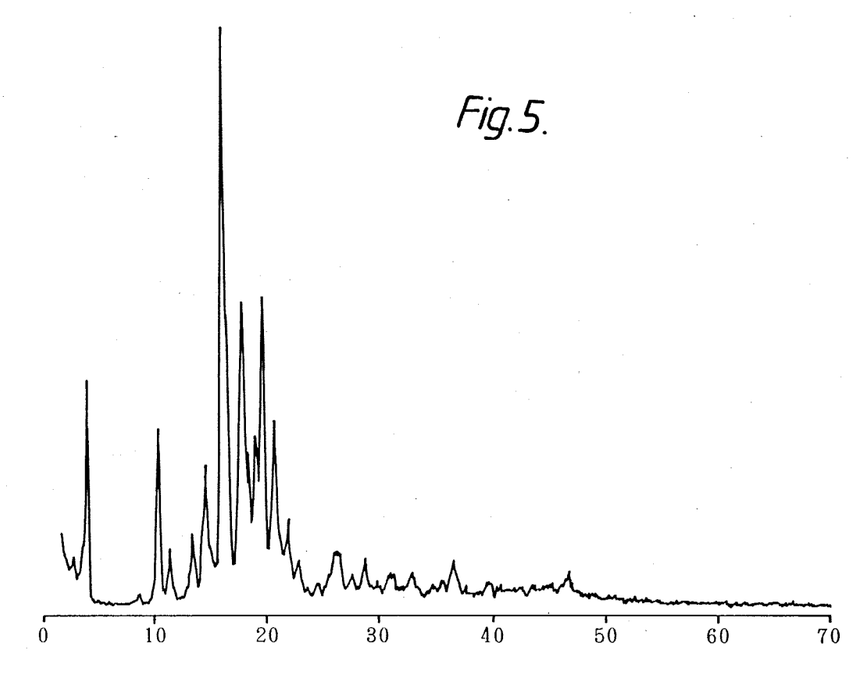
FIG. 5 is that of the crystal (mixture of αβ-crystal and δ-crystal) obtained in Comparative example 1.

In the above Comparative examples, the Cu-K$_\alpha$ X-ray diffraction patterns of the white crystals obtained in Comparative examples 1, 2 and 5 were as shown in FIGS. 5, 2 and 3, respectively.

The white crystals obtained in Comparative examples 3 and 4 had the same X-ray diffraction pattern as shown in FIG. 2.

TABLE 3

| | Weight of crystal (g) | Purity of desired product (wt. %) | Recrystallization solvent | Crystallization temperature (°C.) | Time required for crystallization (hr) | Color | Melting point (°C.) |
|---|---|---|---|---|---|---|---|
| Example | | | | | | | |
| 1 | 45.7 | 98.0 | Methanol/water | 50 | 2 | White | 124–126 |
| 2 | 45.3 | 97.8 | Ethanol/water | 50 | 2 | White | 123–125 |
| 3 | 46.0 | 97.5 | Isopropanol/water | 50 | 2 | White | 123–125 |
| 4 | 46.5 | 97.5 | n-Hexanol/water | 50 | 2 | White | 122–126 |
| 5 | 46.8 | 97.8 | 2-Ethylhexanol | 80 | 3 | White | 120–124 |
| 6 | 46.6 | 97.3 | Glycerin | 80 | 3 | White | 120–123 |
| 7 | 46.6 | 97.2 | Triethylene glycol | 80 | 3 | White | 120–125 |
| 8 | 44.0 | 98.5 | Acetone/water | 50 | 3 | White | 123–126 |
| 9 | 44.8 | 98.0 | Methyl isobutyl ketone/water | 50 | 3 | White | 123–125 |
| 10 | 43.7 | 98.2 | Acetonitrile/water | 50 | 3 | White | 123–125 |
| 11 | 43.3 | 97.9 | 1,4-Dioxane/water | 50 | 3 | White | 122–124 |
| 12 | 44.5 | 97.5 | Tetrahydrofuran/water | 50 | 3 | White | 122–125 |
| 13 | 44.2 | 98.1 | N,N—dimethylformamide/ | 50 | 3 | White | 122–125 |

TABLE 3-continued

| | Weight of crystal (g) | Purity of desired product (wt. %) | Recrystallization solvent | Crystallization temperature (°C.) | Time required for crystallization (hr) | Color | Melting point (°C.) |
|---|---|---|---|---|---|---|---|
| 14 | 44.7 | 98.2 | N,N—dimethylacetamide/water | 50 | 3 | White | 121–124 |
| 15 | 42.8 | 97.9 | Pyridine/water | 50 | 3 | White | 120–123 |
| 16 | 46.0 | 98.5 | Cyclohexane | 50 | 15 | White | 120–125 |
| 17 | 40.5 | 97.3 | Cyclohexane | 50 | 15 | White | 120–124 |
| 18 | 41.9 | 97.5 | Cyclohexane | 50 | 15 | White | 120–124 |
| 19 | 46.2 | 97.1 | Methylcyclopentane | 50 | 15 | White | 119–124 |
| 20 | 45.9 | 97.5 | Methylcyclohexane | 50 | 15 | White | 118–123 |
| 21 | 46.1 | 98.0 | Cyclooctane | 50 | 15 | White | 119–125 |
| 22 | 43.0 | 98.5 | Toluene | Room temperature | 8 | White | 122–125 |
| 23 | 43.5 | 98.0 | Ethylbenzene | Room temperature | 8 | White | 121–125 |
| 24 | 43.9 | 97.7 | Cumene | Room temperature | 8 | White | 121–124 |
| 25 | 44.7 | 98.1 | p-Cymene | Room temperature | 8 | White | 120–124 |
| 26 | 45.0 | 97.4 | Ethyl acetate/n-hexane | Room temperature | 8 | White | 119–123 |
| 27 | 44.1 | 97.3 | n-Butyl acetate/n-hexane | Room temperature | 8 | White | 118–123 |
| 28 | 45.6 | 97.2 | Di-n-butyl phthalate/n-hexane | Room temperature | 8 | White | 119–123 |
| 29 | 44.3 | 97.9 | Chloroform/n-hexane | Room temperature | 8 | White | 120–124 |
| 30 | 46.0 | 97.5 | 1,1,2,2-Tetrachloroethane/n-hexane | Room temperature | 8 | White | 118–124 |
| Comparative example | | | | | | | |
| 1 | 44.3 | 97.8 | Methanol/water | 30 | 5 | White | 102–120 |
| 2 | 46.1 | 98.3 | Cyclohexane | 30 | 6 | White | 102–107 |
| 3 | 37.6 | 93.5 | Cyclohexane | 30 | 24 | Pale yellow | 95–99 |
| 4 | 39.4 | 93.8 | Cyclohexane | 30 | 24 | Pale yellow | 95–100 |
| 5 | 48.0 | 96.7* | n-Hexane | 50 | 6* | Pale yellow | 93–101 |

*Solidified at the bottom of apparatus and did not disperse.

What is claimed is:

1. Hydroxyphenylpropionic acid ester represented by the structural formula

-continued having a crystalline structure which, when subjected to Cu-K$_\alpha$ X-ray diffraction, shows sharp X-ray diffraction peaks at angles of diffraction, $2\theta = 4.2°$ and $2\theta = 10.6°$ and having a melting point in the range of from about 124° C. to about 127° C.

* * * * *